United States Patent
Fujikawa et al.

(10) Patent No.: US 6,479,054 B1
(45) Date of Patent: Nov. 12, 2002

(54) PROCESS FOR OBTAINING GENISTIN-RICH ISOFLAVONE COMPOSITION

(75) Inventors: Yoko Fujikawa, Ibaraki (JP); Tetsuji Tomita, Ibaraki (JP); Yasuko Yoshizawa, Chiba (JP); Tsuneya Yatake, Ibaraki (JP)

(73) Assignee: Showa Sangyo Co., Ltd., Tokyo (JP)

( * ) Notice: Subject to any disclaimer, the term of this patent is extended or adjusted under 35 U.S.C. 154(b) by 0 days.

(21) Appl. No.: 09/787,617

(22) PCT Filed: Sep. 21, 1999

(86) PCT No.: PCT/JP99/05139

§ 371 (c)(1),
(2), (4) Date: Jun. 18, 2001

(87) PCT Pub. No.: WO00/17217

PCT Pub. Date: Mar. 30, 2000

(30) Foreign Application Priority Data

Sep. 21, 1998 (JP) ............................. 10-283580

(51) Int. Cl.[7] .......................... A01N 65/00; A61K 35/76
(52) U.S. Cl. ..................... 424/195.1; 424/756; 536/124; 536/127; 536/128; 536/4.1; 536/8; 435/200; 514/456
(58) Field of Search ................................. 536/124, 127, 536/128, 4.1, 8; 424/195.1, 756; 435/200; 514/456

(56) References Cited

U.S. PATENT DOCUMENTS

| | | | |
|---|---|---|---|
| 5,320,949 A | * 6/1994 | Shen .......................... 435/68.1 |
| 5,702,752 A | 12/1997 | Gugger et al. | |
| 5,789,581 A | 8/1998 | Matsuura et al. | |
| 5,792,503 A | 8/1998 | Gugger et al. | |
| 5,821,361 A | * 10/1998 | Waggle et al. .............. 536/128 |
| 5,990,291 A | * 11/1999 | Waggle et al. ................. 536/8 |
| 6,033,714 A | 3/2000 | Gugger et al. | |
| 6,261,565 B1 | * 7/2001 | Empie et al. ............. 424/195.1 |
| 6,323,018 B1 | * 11/2001 | Waggle et al. .............. 435/200 |

FOREIGN PATENT DOCUMENTS

| | | | |
|---|---|---|---|
| EP | 647 408 | * | 4/1995 |
| EP | 0 647 408 A1 | | 4/1995 |
| EP | 0 795 553 A1 | | 9/1997 |
| JP | 59-137421 A | | 8/1984 |
| JP | 62-126186 A | | 6/1987 |
| JP | 07173148 A | | 7/1995 |
| JP | 07238089 A | | 9/1995 |
| JP | 08231533 A | | 9/1996 |
| JP | 08283283 A | | 10/1996 |
| JP | 09059166 A | | 3/1997 |
| JP | 09255570 A | | 9/1997 |
| JP | 10-23878 A | | 1/1998 |

OTHER PUBLICATIONS

Walz, "Isoflavone and Saponin Glucosides in Soya Hispida." Annalen der Chemie, vol. 489: 118–155 (1932).*
Anthony et al., Amer. Inst. Nutrition 126:43–50 (1996).
Arjimandi et al., Amer. Inst. Nutrition 126:161–167 (1996).
Author Unknown, "Physiological Functions and Utilization of Isoflavone . . . " Shokuhin & Kaihatsu 31(6):44–47 (1996).
Kihara, K., Nippon Shoyu Kenkyusho Zasshi 15(5):171–176 (1989).

* cited by examiner

Primary Examiner—Samuel Barts
Assistant Examiner—Devesh Khare
(74) Attorney, Agent, or Firm—Wolf, Greenfield & Sacks, P.C.

(57) ABSTRACT

A process for simply and efficiently obtaining an isoflavone composition having a high ratio of genistin, which useful as a food material and the like, wherein in the process for obtaining genistin from a isoflavone inclusion, genistin is selectively precipitated by applying pH adjustment to isoflavone containing liquid.

7 Claims, 1 Drawing Sheet

Change of isoflavone amounts in a solution by pH

Change of isoflavone amounts in a solution by pH

US 6,479,054 B1

PROCESS FOR OBTAINING GENISTIN-RICH ISOFLAVONE COMPOSITION

RELATED APPLICATIONS

This application is a national stage filing under 35 U.S.C. §371 of PCT application PCT/JP99/05139, filed Sep. 21, 1999. Foreign priority benefits are claimed under 35 U.S.C. §119(a)–(d) or 35 U.S.C. §365(b) of Japan application number 10-283580, filed Sep. 21, 1998.

TECHNICAL FIELD OF THE INVENTION

The invention relates to a process for obtaining genistin from isoflavone inclusions.

BACKGROUND ART

In accordance with the change of lifestyle and the advance of the aging, the increase of lifestyle-related diseases has been a big problem. Prevention against malignant neoplasm, cardiac disease and cerebrovascular disease, the present three major cause of death, and bone fracture by osteoporosis which can be a cause of a bedridden state is strongly desired. For the prevention against them, a well balanced daily diet is important, though together with this it has been required to take actively a diet and food composition in which their prevention effects are recognized.

In such a situation, the attention to isoflavones, as a functional factor in foods is rising.

That is, isoflavones are recently shown to have a preventive and therapeutic effects for hyperlipidemia (J. Nutr. 126: 43–50 (1996); JP, 9-255570, A) and a preventive and therapeutic effects for osteoporosis (J. Nutr. 126: 161–167 (1996); JP, 8-231533, A).

Further, from the results of the epidemiological investigation and the animal experiments, it has been clarified that more intake of isoflavone results in higher bone density and lower cancer incidence (Shokuhin & Kaihatsu, vol. 31 No. 6: 44–47 (1996)).

Thus, it has been confirmed that isoflavones have a number of pharmacological effects such as an estrogen, antioxidant or anticancer actions.

Consequently, it is needed to provide isoflavones at lower costs.

Now, it is well known that in soybeans are contained daizein, genistein and its glycoside, daidzin, genistin, and malonate or acetate of each isoflavone glycoside, and conventionally isoflavones are obtained from soybeans.

As a conventional method to obtain isoflavones from soybeans, the followings are illustrated.

(1) JP, 4-21670, B

Extraction liquid of soybeans as it is or that after evaporation of solvent is contacted with a non-polar porous synthetic adsorption resin having a huge network structure to adsorb isoflavone derivatives, and then eluted from said synthetic resin using organic solvents or a mixed solvent of organic solvents and water, to obtain a solution containing isoflavone derivatives such as genistin.

(2) JP, 4-34526, B

From "broth", "Yu", "whey", etc., physiologically active substances mainly consisting of saponins, flavonoids, isoflavonoids and glycosides thereof are obtained by adsorption-desorption with charcoal, active carbon or an active resin, wherein elution is carried out using an aqueous ethanol solution as the eluting solvent and the eluate is concentrated under reduced pressure to obtain a concentrate.

For example, from adsorbents of the active resin for "Yu", a waste liquid in a tofu factory, are obtained respectively one consisting of 69% isoflavonoid type components with genistein as the main component and 8% saponin type components by elution with 60–95% ethanol, and one consisting of 81% isoflavonoid type components with genistein as the main component and 12% saponin type components by elution with 5–10N acetic acid.

(3) JP, 7-173148, A

Shed soybeans are immersed in warm water of 50° C. (adjusted to pH 9 by alkali), and the immersion liquid is added with synthetic resin (Diaion HP-20), stirred, and added with 1N-ammonia water. The resin adsorbent is eluted, and the elution liquid is concentrated under reduced pressure to give a syrup concentrate. The concentrate is extracted under reflux adding chloroform, and an extraction residue is recovered, added with 4% HCl methanolic solution, hydrolyzed at 100° C. under reflux for 6 hr. A hydrolyzate is concentrated under reduced pressure, washed thoroughly with distilled water, followed by drying the residue to give brown solid of an isoflavone mixture, with daizein and genistein as the main components.

(4) JP, 8-231533, A

This relates to a novel flavonoid glycoside, a therapeutic agent for osteoporosis comprising the flavonoid glycoside and an edible composition, and the flavonoid glycoside is obtained in the following way.

Defatted natto is extracted with methanol, concentrated to dryness by a rotary evaporator to give an extract. The methanolic extract is dissolved in distilled water, adsorbed to a column packed with a synthetic adsorbent (Diaion HP-20 (trade name); manufactured by Mitsubishi Kasei Co., Ltd.), eluted with 30% methanol and 70% methanol successively. The 70% methanol eluate is concentrated and chromatographed for separation using Sephadex LH-20 (manufactured by Pharmacia Co., Ltd.), making methanol as the eluting solvent to give a fraction containing various 6"-O-succinylisoflavones such as 6"-O-succinylgenistin.

(5) JP, 8-283283, A

Soybean is extracted with water, and the water extraction liquid is adsorbed to an adsorption resin to adsorb malonylisoflavone glycosides in the extraction liquid, followed by elution with an aqueous alcohol solution to obtain malonylisoflavone glycosides. The obtained malonylisoflavone glycoside solution is subjected to a heat treatment and/or an alkali treatment to lead to an isoflavone glycoside solution which is subjected to an acid treatment or an enzyme treatment to obtain isoflavone aglycons.

For example, water extraction liquid of 3 kg of shed soybeans is adsorbed and eluted with an aqueous methanol solution. The obtained eluate is analyzed by high-performance liquid chromatography to obtain each concentrate containing 1.61 g of malonyldaidzin and 1.76 g of malonylgenistin respectively.

(6) JP, 9-59166, A

This relates to an epidermal growth accelerating agent wherein malonylispoflavone glycos ides are effective components. The malonylisoflavone glycosides of effective components are obtained as follows.

20 L of warm water extract of shed soybeans is adjusted to pH 4.0 by hydrochloric acid, let stand for 2 hr, followed by addition of a filtration auxiliary agent and by suction filtration on Büchner funnel. The filtrate is passed through column packed with active carbon at the flow rate of 1.5 L/hr to adsorb malonylisoflavone glycosides, followed by wash of the column with 3 L of 1% ammonia water and subsequent elution with 5 L of 50% aqueous ethanol solution containing 1% ammonia. The obtained eluate is concentrated under reduced pressure at 50° C. to obtain 500 ml of concentrate containing 1.23 g of malonyldaidzin and 1.05 g of malonylgenistin.

(7) JP, 10-23878, A

This is a process for recovering isoflavones from an aqueous soy molasses feed stream, and comprises a step of heating the above feed stream to temperature for solubilization of genistin, a step of separating purified genistin products in a permeate of the above starting material by subjecting the above heated feed stream to ultrafiltration, a step of accelerating crystallization of genistin by cooling the above feed stream permeate treated by the above filtration, and a step of separating genistin by centrifugation or filtration of the above cooled permeate.

By inspecting the above conventional processes the followings can be mentioned.

In the invention (1), a solution containing daidzin, glycitin, genistin, daizein, genistein, etc., is obtained as an eluate, but a separation recovery of genistin from said eluate is not carried out.

In the invention (2), it is described that isoflavonoid type components consisting of 69–81% of genistein as the main component were obtained, but the obtainment of genistin is unclear.

In the invention (3), a chlorine containing organic solvent is used as the extracting solvent.

In the invention (4), the separation recovery of glycosides from an eluate is carried out by chromatography.

In the invention (5), the eluate is subjected to high-performance liquid chromatography as it is, and malonyldaidzin and malonylgenistin are separately obtained.

In the invention (6), the eluate is concentrated under reduced pressure to obtain a concentration liquid containing malonylgenistin.

In the invention (7), a precipitate of genistin is obtained from ultrafiltration liquid using the solubility difference due to temperature.

The above conventional processes adopt mere concentration under reduced pressure, a tedious separation means such as chromatography, a separation means such as crystallization by slow cooling which consumes time, and a chlorine containing organic solvent, etc. These processes are confronted with problems in the points such as the content of genistin, the tedious separation means, the prolonged procedure by the slow cooling, and the food safety. Therefore, the present situation is that there is still no practical process for obtaining an isoflavone composition high in the genistin content.

DISCLOSURE OF THE INVENTION

Consequently, the problem of the invention is to obtain, from liquid containing isoflavones, simply and efficiently an isoflavone composition high in the genistin content which is useful for food materials and the like.

The inventors made extensive researches to solve the above problem, and found out that genistin could efficiently be separated by adjusting the pH of an eluate containing isoflavones which was obtained by an adsorption-desorption treatment of soybean extraction liquid or its process treatment liquid, and finally accomplished the invention as the result of continuous further researches.

The invention is as follows:

(1) A process for obtaining an isoflavone composition essentially comprising genistin, characterized by applying a pH adjustment to isoflavone containing liquid to selectively precipitate genistin.

(2) A process for obtaining an isoflavone composition essentially comprising genistin according to the above (1) wherein the pH adjustment is to make the pH of an isoflavone containing liquid not more than 9.5.

(3) A process for obtaining an isoflavone composition essentially comprising genistin according to the above (1) wherein the pH adjustment is to make the pH of an isoflavone containing liquid not less than 10 and then to make not more than 9.5.

(4) A process for obtaining an isoflavone composition essentially comprising genistin according to the above (1), (2) or (3), wherein the isoflavone containing liquid is obtained eluting with an eluting agent, after isoflavone components in an extraction liquid of an isoflavone inclusion are adsorbed to an adsorption agent.

(5) A process for obtaining an isoflavone composition essentially comprising genistin according to the above (1), (2), (3) or (4) wherein the isoflavone containing liquid is derived from soybeans.

(6) A process for obtaining an isoflavone composition essentially comprising genistin according to the above (4) or (5) wherein the eluting agent is an aqueous solvent or a mixed solvent of aqueous solvents with organic solvent.

(7) A process for obtaining an isoflavone composition essentially comprising genistin according to the above (6) wherein the aqueous solvent of the eluting agent is an aqueous alkaline solution.

The invention is based on the novel finding that the solubility of genistin in an isoflavone containing eluate is greatly influenced by a pH, wherein its solubility changes suddenly at the boundary of the pH of 10, that is, extremely high at pHs of not less than 10 and extremely low at the pHs of not more than 9.5 (see FIG. 1; in FIG. 1, using a similar method with that of the example 2, the eluting liquid (pH 9.7) was used, letting only the eluting condition for the adsorbent on the resin from 0.25N to 0.5N. It was adjusted to an optional pH by 2N-HCl, followed by removal of the precipitate by centrifugation. Concentrations of isoflavones in a supernatant are shown, making each isoflavone concentration at the time of elution 100.).

Accordingly, the particular characteristic of the invention is in the point, which the pH of an eluate containing isoflavones which is obtained by an adsorption-desorption treatment of soybean extraction liquid or its process treatment liquid is adjusted in two steps, that is, first, (1) the pH of said eluate is made not less than 10, dissolving genistin completely, then (2) the pH of said eluate is made not more than 9.5, preferably 9.5–3, letting genistin precipitate completely to obtain simply and efficiently an isoflavone composition high in the genistin content.

Further, in case of using a conventional eluting liquid as the eluting liquid, it is necessary to adjust the above pH in two steps, though in case of using an alkaline aqueous solution as said liquid in which its pH is not less than 10, the above (1) step treatment is not especially necessary.

Accordingly, the invention is of great value in the point that an isoflavone composition high in the genistin content can be obtained simply and efficiently by an extremely simple means, that is, a pH adjustment.

Since in the invention a tedious separation procedure such as chromatography is not especially necessary, it is economically advantageous.

Further, since in the invention the precipitation of an aimed substance occurs without carrying out a slow cooling as in a usual crystallization, it is also advantageous in time.

MODE FOR CARRYING OUT THE INVENTION

Figure 1:
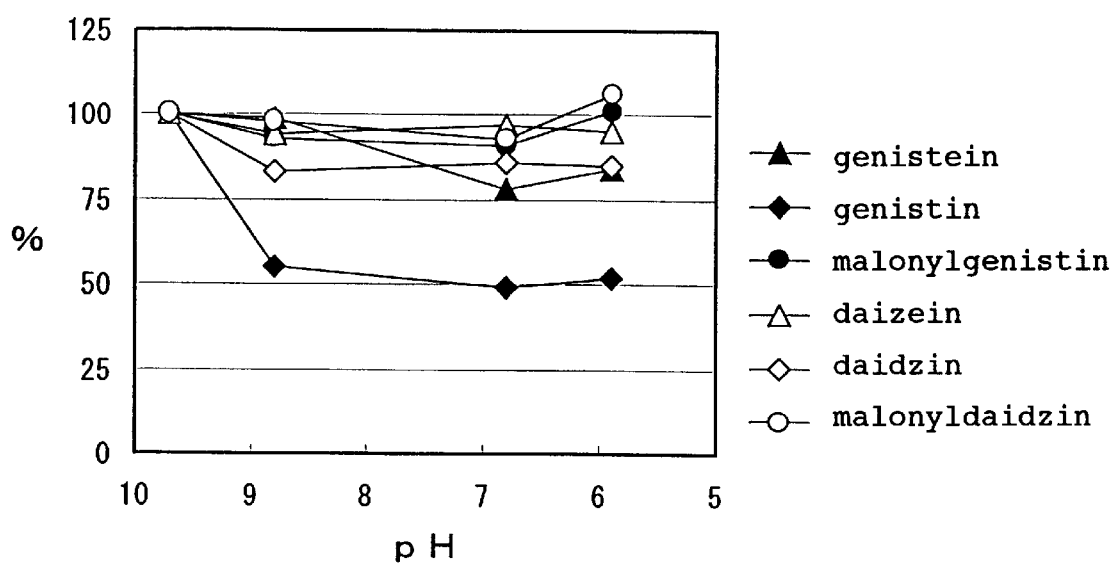
FIG. 1: The relationship between the pH change and the isoflavone concentration.

In the following the invention is explained in more detail.

(1) Preparation of a Solution Containing Isoflavones

A solution containing isoflavones can be any extraction liquid of plants containing isoflavones, though it is preferred to use extraction liquid of soybeans containing isoflavones particularly in a large amount.

Illustrative of an extraction liquid of soybeans are those wherein milled soybeans, shed soybeans, defatted soybeans, soybean flour, soybean hypocotyl, defatted soybean hypocotyl, or the like are extracted by aqueous solvents, organic solvents, a mixed solvent of aqueous solvents with organic solvents or the like.

Further, process waste liquid such as "immersion waste", "broth", "Yu", "whey" or the like produced in a step to manufacture processed products of soybeans, for example, such as soybean tofu, soybean paste, soy sauce, natto, soy milk, soybean sprouts or the like can also be used.

For example, a process for obtaining an aqueous extraction liquid includes a process wherein shed soybeans are immersed for 2–4 hr in warm water (45–65° C.), adjusted to a pH of not more than 10.0, preferably 7.5–9 by alkali such as sodium hydroxide, followed by water extraction of an immersed solution obtained after removal of the immersed soybeans.

Further, in case of defatted soybeans, ground materials of defatted soybeans is extracted with water or alkaline water, followed by removal of the insoluble residue, and liquid, that is, soybean whey is preferred, in which separated soy proteins obtained by acid precipitation around pH of 4.3 of extraction liquid with an acid such as hydrochloric acid is removed. Ground materials of defatted soybeans is extracted with acidic water of the pH of 3.0–6.0, and the obtained liquid after removal of the insoluble residue can also be used.

As an organic solvent in organic solvent extraction can be used is methanol, ethanol or the like.

As to extraction liquid of soybeans, protein is preferably removed if necessary. As a process for removing proteins there are an ultrafiltration membrane process and an acid treatment process. In an acid treatment process, the extraction liquid is adjusted with hydrochloric acid to around the pH of 4–5, and precipitated proteins are preferably removed by a means such as centrifugation or filtration.

(2) Separation Recovery of Isoflavones

Separation recovery of genistin can be carried out from extraction liquid of soybeans, processed waste liquid of soybeans or the like as it is, but it is preferable to make separation recovery of isoflavones beforehand by an adsorption-desorption process using an adsorption agent described in the following.

a) Adsorption

As to adsorption, extraction liquid as it is or after removal of solvent may be contacted with an adsorption agent.

In the case that there is a difference of acidity or basicity in extraction liquid or processed waste liquid of soybeans, it is preferred that a suitable acidifying or alkalizing agent can appropriately be added to keep the condition around the pH of 3.5–5.0 in order to increase the adsorption ratio of isoflavone to an adsorption agent. The acidifying agents in this case include acetic acid, hydrochloric acid, etc., and the alkalizing agents include sodium hydrogencarbonate and sodium hydroxide.

As the adsorption agents used is a synthetic adsorption agent, active carbon, alumina or the like, and illustrated, for example, "Diaion HP Resin" (Mitsubishi Kasei Co., Ltd.), "Amberlite XAD Resin" (Rohm & Haas Co., Ltd.), "Duolite S Resin" (Diamond Shamrock Co., Ltd.), Purified Shirasagi Active Carbon (Takeda Chemical Industries Co., Ltd.), Active Alumina (Wako Pure Chemical Industries Co., Ltd.), and the like. As the synthetic adsorption agents that also can be used are those modified with a functional group such as an ion-exchange group.

As to the contact of treatment liquid (an extraction liquid or the like) with an adsorption agent, either a batch or column process may be used. In case of the batch process, it is carried out by a conventional means such that an adsorption agent is placed in an appropriate container and treated stirring if necessary. In case of the column process, it can be achieved by a conventional means, and an eluting rate can appropriately be selected considering various conditions such as the size of the column and the eluting solvent used. Since the above batch and column processes are both physical adsorption, preferable temperature is room temperature.

b) Desorption

Desorption is carried out by elution of isoflavones adsorbed to an adsorption agent. As an eluting process, either a batch or column process may be used.

As eluting solvent that can be used are organic solvents or a mixed solvent of organic solvents and aqueous solvents, or the like. The type, concentration, amount and the like of the eluting solvent is appropriately selected considering various conditions such as whether a batch process or a column process, and the type and amount of the adsorption agent used.

Illustrative of organic solvents are methanol, ethanol, isopropanol, acetone and the like, preferably alcohols, more preferably ethanol.

Further, since in separation recovery of genistin of the next step (3) pH adjustment is carried out, not a conventional eluting agent but an alkaline solution such as an aqueous sodium hydroxide solution is advantageously used as the eluting agent.

(3) Separation Recovery of Genistin

Since various components are contained in the eluate containing the above isoflavones, a particular means for separation and purification is necessary in order to obtain the aimed isoflavone component, that is, genistin.

That is, the invention is to obtain efficiently and simply an isoflavone composition containing genistin in a high concentration by means of a pH adjustment as the following.

Adjustment of pH of the eluate containing isoflavones is carried out in two steps. First, (1) the pH of said eluate is made not less than 10, having this completely dissolved by raising the solubility of genistin, and subsequently, (2) the pH of said eluate is made not more than 9.5, having this completely precipitate by lowering the solubility of genistin to give separation recovery of the aimed genistin at a high concentration.

In the case that an organic solvent is contained in the eluting agent, it is preferred that the organic solvent is distilled off before the pH adjustment of (2). A concentration step can be added between step (1) and step (2) if necessary.

Further, in the isoflavone separation in the above steps, if the eluting agent not a conventional eluting agent but an alkaline aqueous solution or alkaline water containing an organic solvent is used, wherein in the case that the pH of an eluate is not less than 10, pH adjustment of the above step (1) is not especially necessary as described above.

After pH adjustment the liquid temperature can be room temperature, though an isoflavone composition consisting of genistin can be obtained in a high yield by keeping at a low temperature (4–10° C.).

Further, in the case that a genistin inclusion of a higher purity is desired, it can be purified and isolated by a conventional means for separation purification (for example, countercurrent distribution, recrystallization, column chromatography, etc.).

Further, the adsorption agent used in a process for obtaining the solution containing isoflavones in the invention can repeatedly be used by washing regeneration with a suitable organic solvent (for example, an alcohol type, acetone type organic solvent, etc.) or an alkaline agent (for example, sodium hydroxide, potassium hydroxide, etc.), and thus it is very economical.

(4) Utility

It is known that isolavones show physiological activity in the state of aglycons in which a sugar chain is detached, though aglycons are inferior to glycoxides in the points of a taste characteristic and solubility, which causes an obstacle in case of their utilization for foods and the like. Since a sugar chain of glycoxides is cut in a digestive tract, there is no difference compared with aglycons in terms of physiological activity.

Further, since genistin is $1/10$–$1/5$ in an astringent taste compared with daidzin (Syokuhin Kogyo Nov. 30, 1997: 24–30), isoflavones good in taste characteristics, can be obtained by concentrating genistin.

As described above, since genistin has various excellent characteristics such as osteoporosis prevention and cancer prevention, extremely useful functional foods can be obtained by adding the isoflavone composition containing genistin of the invention to foods.

Illustrative of the uses are, for example, foods such as drinks, sweets, processed foods and spices, drugs, starting materials for drugs, and cosmetics.

In the following explained is the invention in more detail by way of examples, but it is to be understood that the invention is not limited in any way. In the following examples, "%" means "% by weight" unless otherwise specified.

EXAMPLE 1

100 g of low temperature defatted soybean flour was added with 1 L of 0.2% (v/v) phosphoric acid solution, stirred, followed by adjustment of the pH to 4.7, and extracted at 50° C. for 60 min. Extraction liquid was recovered by centrifugation (8,800×g, 15 min).

The obtained soybean whey was added with Diaion HP-20 (20 ml) and stirred for 2 hr. The resin was washed with water to wash out non-adsorbed components, and then an adsorbent to the resin was eluted adding 100 ml of 0.5N sodium hydroxide solution. After the pH of the obtained eluate was made to 8 by 1N hydrochloric acid, its temperature being kept at 4° C. for 2 hr, it was recovered by centrifugation and, dried at 50° C. under reduced pressure to obtain a solid (30 mg) comprising genistin. The isoflavone content of the obtained solid was 95%, and the ratio of genistin against the total isoflavones was 85%.

EXAMPLE 2

100 g of low temperature defatted soybean flour was added with 1 L of 0.2% (v/v) phosphoric acid solution, stirred, followed by adjustment of the pH to 4.7, and extracted at 50° C. for 60 min. Extraction liquid was recovered by centrifugation (8,800×g, 15 min).

The obtained soybean whey was filtered through an ultrafiltration membrane (NTU-3150; manufactured Nitto Denko Corporation) of fractionation molecular weight 30,000 to give 750 ml of permeate. This was passed through a column packed with Diaion HP-20 (20 ml). The resin was washed with water (40 ml) to wash out non-adsorbed components, and then an adsorbent to the resin was eluted passing 80 ml of 0.25N sodium hydroxide solution. The obtained eluate was neutralized by 1N hydrochloric acid, and kept at temperature 4° C. for 2 hr. Then, the resulting precipitate was recovered by centrifugation, dried at 50° C. under reduced pressure to obtain a solid (53 mg) comprising of genistin. The isoflavone content of the obtained solid was 98%, and the ratio of genistin against the total isoflavones was 87%.

Further, a solid (1700 mg) from the eluate giving the above adsorbent to resin was analyzed as reference, showing the isoflavone content to be 6.1% wherein its isolavone composition was 53% of genistin (including malonylgenistin), 38% of daidzin (including malonyldaidzin) and 9% of the others.

Comparative Example 1

The eluate of the adsorbent to resin obtained in the example 2 was kept alone at 4° C. overnight. Then, the resulting precipitate was recovered by centrifugation, dried to obtain a solid (9 mg). The isoflavone content of the obtained solid was 98%, and the ratio of genistin against the total isoflavones was 90%.

From this result, evidently, compared with the prior process, there is no difference in the quality of isoflavone composition obtained by the process of the invention, and the sixfold amount can be obtained in a short time.

EXAMPLE 3

100 g of low temperature defatted soybean flour was added with water of 50° C. (1 L), adjusted to the pH to 8.0 by alkali, and extracted for 30 min under stirring. An extraction liquid was recovered by centrifugation (8,800×g, 15 min).

The extraction liquid was added with hydrochloric acid under stirring to adjust the pH to 4.5, allowed to stand for 1 hr, added with a filtration auxiliary agent, and filtered by suction to give 800 ml of extraction whey. This was passed through a column packed with Diaion HP-20 (20 ml). The resin was washed with water (40 ml) to wash out non-adsorbed components, and then an adsorbent to the resin was eluted passing 80 ml of 50% ethanolic solution containing 0.25N sodium hydroxide. The eluate was evaporated under reduced pressure to remove ethanol, and then neutralized by 1N hydrochloric acid. A resulting precipitate was recovered, lyophilized to give a solid (18 mg) comprising genistin. The isoflavone content of the obtained solid was 82%, and the ratio of genistin against total isoflavones was 79%.

EXAMPLE 4

Extraction whey (800 ml) obtained in the same way as the example 3 was passed through a column packed with Diaion HP-20 (20 ml). The resin was washed with water (40 ml), and then eluted with 30% ethanol and 70% ethanol successively. The 70% ethanol eluting fraction was added with 1N sodium hydroxide solution and then evaporated under reduced pressure to remove ethanol. This liquid was neutralized by 1N hydrochloric acid and kept at 4° C. for 2 hr. The resulting precipitate was recovered, dried to give a solid (20 mg) comprising genistin. The isoflavone content of the obtained solid was 97%, and the ratio of genistin against the total isoflavones was 92%.

EXAMPLE 5

200 g of low temperature defatted soybean flour was added with 2 L of 0.2% (v/v) phosphoric acid solution, stirred, followed by adjustment of the pH to 4.7, and extracted at 50° C. for 60 min. The extraction liquid was recovered by centrifugation.

The obtained soybean whey was filtered through an ultrafiltration membrane (manufactured Nitto Denko Corporation) having fractionation molecular weight of 30,000 to give 1500 ml of permeate. This was passed through a column packed with Diaion HP-20 (40 ml). The resin was washed with water (80 ml) to wash out non-adsorbed components, and then an adsorbent to the resin was eluted by passing 160 ml of 0.25N sodium hydroxide solution. The obtained eluate was equally divided into two 80 ml fractions, their pH being adjusted by 1N hydrochloric acid to 5.0 and 3.0. Each resulting precipitate was recovered and dried under reduced pressure at 50° C.

In case of the pH of 5.0, a solid (57 mg) was obtained. The isoflavone content of the obtained solid was 93%, and the ratio of genistin against the total isoflavones was 85%.

In case of the pH of 3.0, a solid (64 mg) was obtained. The isoflavone content of the obtained solid was 87%, and the ratio of genistin against the total isoflavones was 81%.

INDUSTRIAL APPLICABILITY AND EFFECT OF THE INVENTION (1) The invention can obtain simply and efficiently an isoflavone composition high in the genistin content by an extremely simple means, that is, pH adjustment.

(2) In particular, since tedious separation procedures such as chromatography are not especially necessary, it is economically advantageous.

(3) Since precipitation of the aimed substance occurs without carrying out time consuming crystallization by slow cooling, it is also advantageous in time.

(4) Since, in particular, it is not necessary to use a chlorine containing organic solvent as an extracting solvent, there is no problem in the food safety, and an the isoflavone composition of the invention is applicable to foods.

(5) Since genistin is $1/10$–$1/5$ in an astringent taste compared with daidzin, isoflavones good in taste characteristics can be obtained by concentrating genistin.

(6) Since genistin has various excellent characteristics such as osteoporosis prevention, hyperlipidemia prevention and cancer prevention, extremely useful functional foods can be obtained by the addition of the isoflavone composition containing genistin of the invention to foods.

What is claimed is:

1. A process for obtaining an isoflavone composition essentially comprising genistin by applying pH adjustment to an isoflavone containing liquid to selectively precipitate genistin, wherein the pH adjustment is to make the pH of He isoflavone containing liquid not less than 10 and then to make the pH of the isoflavone containing liquid not more than 9.5.

2. A process for obtaining an isoflavone composition essentially comprising genistin according to claim 1 wherein the isoflavone containing liquid is obtained by eluting with an eluting agent, after isoflavone components in an extraction liquid of an isoflavone inclusion are adsorbed to an adsorption agent.

3. A process for obtaining an isoflavone composition essentially comprising genistin according to claim 2, wherein the eluting agent is an aqueous solvent or a mixed solvent of aqueous solvents with organic solvent.

4. A process for obtaining an isoflavone composition essentially comprising genistin according to claim 3, wherein the aqueous solvent of the eluting agent is an aqueous alkaline solution.

5. A process for obtaining an isoflavone composition essentially comprising genistin according to claim 1 or 2, wherein the isoflavone containing liquid is derived from soybeans.

6. A process for obtaining an isoflavone composition essentially comprising genistin according to claim 5, wherein the eluting agent is an aqueous solvent or a mixed solvent of aqueous solvents with organic solvent.

7. A process for obtaining an isoflavone composition essentially comprising genistin according to claim 6, wherein the aqueous solvent of the eluting agent is an aqueous alkaline solution.

\* \* \* \* \*

UNITED STATES PATENT AND TRADEMARK OFFICE
CERTIFICATE OF CORRECTION

PATENT NO.   : 6,479,054 B1
DATED        : November 12, 2002
INVENTOR(S)  : Fujikawa et al.

It is certified that error appears in the above-identified patent and that said Letters Patent is hereby corrected as shown below:

Column 10,
Line 14, delete "He" and replace with -- the --.

Signed and Sealed this

Twenty-fifth Day of March, 2003

JAMES E. ROGAN
*Director of the United States Patent and Trademark Office*